United States Patent [19]
Suzuki et al.

[11] Patent Number: 5,840,883
[45] Date of Patent: Nov. 24, 1998

[54] DEXTRIN ESTER OF FATTY ACIDS AND USE THEREOF

[75] Inventors: Takanao Suzuki, Hiratsuka; Isaburo Amano; Koji Chiba, both of Chiba; Ruka Tofukuji, Tokyo, all of Japan

[73] Assignees: Chiba Flour Milling Co., Ltd., Chiba; Kose Corporation, Tokyo, both of Japan

[21] Appl. No.: 626,469

[22] Filed: Apr. 2, 1996

[30] Foreign Application Priority Data

Apr. 5, 1995 [JP] Japan .................................. 7-080050

[51] Int. Cl.$^6$ .......................... C08B 30/18; C08B 31/02; C08B 31/04
[52] U.S. Cl. .......................... 536/103; 514/58; 514/944; 536/102; 536/107; 536/110
[58] Field of Search .................. 514/58, 944; 536/102, 536/103, 107, 110

[56] References Cited

U.S. PATENT DOCUMENTS

| | | | |
|---|---|---|---|
| 1,959,590 | 5/1934 | Leonard | 260/101 |
| 3,730,925 | 5/1973 | Kovats et al. | 525/54.23 |
| 3,732,206 | 5/1973 | Kovats et al. | 536/108 |
| 3,732,207 | 5/1973 | Kovats et al. | 536/103 |
| 3,919,107 | 11/1975 | Thompson | 510/375 |
| 3,941,771 | 3/1976 | Finley | 536/103 |
| 4,011,392 | 3/1977 | Rudolph et al. | 536/108 |
| 4,029,590 | 6/1977 | Finley | 510/471 |

FOREIGN PATENT DOCUMENTS

| | | |
|---|---|---|
| 50-102470 | 8/1975 | Japan . |
| 52-19834 | 5/1977 | Japan . |
| 56-081301 | 7/1981 | Japan . |
| 61-56115 | 3/1986 | Japan . |
| 63-025372 | 2/1988 | Japan . |
| 63-315294 | 12/1988 | Japan . |
| 01203319 | 8/1989 | Japan . |
| 1-203319 | 8/1989 | Japan . |
| 1-207223 | 8/1989 | Japan . |
| 04049249 | 2/1992 | Japan . |
| 04149116 | 5/1992 | Japan . |
| 06336584 | 12/1994 | Japan . |
| 07277954 | 10/1995 | Japan . |
| 07324177 | 12/1995 | Japan . |

OTHER PUBLICATIONS

*IUPAC Pure and Applied Chemistry,* vol. 67:1364, (1995).

*Primary Examiner*—Marian C. Knode
*Assistant Examiner*—Howard C. Lee
*Attorney, Agent, or Firm*—David G. Conlin; George W. Neuner

[57] ABSTRACT

Disclosed are a dextrin ester of fatty acids in which dextrin has an average saccharide polymerization degree of 3 to 150, the fatty acids comprise a straight chain fatty acid having 8 to 22 carbon atoms and at least one fatty acid selected from the group consisting of branched fatty acids having 4 to 26 carbon atoms, unsaturated fatty acids having 6 to 30 carbon atoms and straight chain saturated fatty acids having 6 or less carbon atoms, and the substitution degree of fatty acids per glucose unit is 1.0 to 3.0; and a gelling agent, a composition and a base comprising the ester, the ester being excellent in thixotropic property, moisture retaining property, emulsifiability, adhesion and dispersibility, and therefore suitably used for cosmetics, printing ink, coatings, etc.

12 Claims, 2 Drawing Sheets

F I G. I.

1

DEXTRIN ESTER OF FATTY ACIDS AND USE THEREOF

FIELD OF THE INVENTION

The present invention relates to a novel dextrin ester of fatty acids and use thereof, and more particularly to a novel dextrin ester of fatty acids obtained by esterifying dextrin with mixed fatty acids comprising a straight chain fatty acid and at least one fatty acid selected from the group consisting of branched fatty acids, unsaturated fatty acids and straight chain saturated fatty acids having 6 or less carbon atoms, a gelling agent comprising said dextrin ester of fatty acids, and a high thixotropic composition comprising said dextrin ester of fatty acids and a liquid oil and/or a solvent.

The dextrin ester of fatty acids of the present invention form a gel having a high thixotropic property which has hitherto never been obtained, by mixing with at least one liquid oil and/or solvent.

The term "thixotropic property" used herein means the property that the viscosity is decreased on application of a definite force and recovered to the original level on removal of the force. This thixotropic property gives smoothness, good spreadability and increased stability to cosmetics, smooth writing to ink, and easy application and no generation of drips to coatings.

BACKGROUND OF THE INVENTION

In order to obtain gel compositions or viscous compositions of liquid oils, methods of using metallic soaps, sucrose esters of fatty acids, organic bentonite, dextrin esters of fatty acids, etc. alone or in combination therewith or in combination with other bases have previously been generally employed.

For example, there have been proposed a method for gelling a liquid fat or oil comprising adding 1% or more of a starch ester of a fatty acid having a substitution degree of ester groups of 1.0 or more to the fat or oil presenting a liquid state at ordinary temperature, heating the resulting mixture at a temperature of 60° C. or more, and then cooling it to ordinary temperature or less (Japanese Patent Examined Publication No. 52-19834), a solid cosmetic comprising a dextrin ester of a fatty acid, N-acylamino acid and a liquid oil containing 30% by weight or more of a polar liquid oil, as essential components (Japanese Patent Unexamined Publication No. 1-207223), an oil make-up cosmetic essentially comprising a dextrin ester of a fatty acid and/or a lipophilic sucrose ester of a fatty acid and organic modified montmorillonite clay (Japanese Patent Unexamined Publication No. 61-56115) and an oil gel base comprising 1% by weight or more of a dextrin ester of mixed fatty acids, said mixed fatty acids consisting of at least two kinds of fatty acids, and a fatty acid occupying the maximum weight ratio being contained in an amount of 80% or less (Japanese Patent Unexamined Publication No. 1-203319).

However, these prior-art techniques suffer from the problems of time-consuming preparation, restriction on the base to be compounded and the ratio thereof, and difficulty in obtaining reproducibility. Above all, it has been difficult to obtain a composition having a high thixotropic property.

For example, the metallic soaps are poor in solubility in liquid oils, and require a high temperature of about 100° C. for dissolution, which causes deterioration in quality of other oils or pigments mixed therewith, cracks and bleeding of oils in the resulting gels, liability to sweat with time, and insufficient gloss and spreadability.

The sucrose esters of fatty acids have the problems of poor gelation, poor transparency and inferior stability at low temperatures.

The starch ester of the fatty acid described in Japanese Patent Examined Publication No. 52-19834 has excellent functionality as the gelling agent. However, the resulting gel is hard and has no thixotropic property. No thixotropic gel is obtained even at low concentrations, and the problem of oil separation with time is encountered. This ester is therefore insufficient as the high thixotropic gelling agent.

In the combination of the dextrin ester of the fatty acid and N-acylamino acid (Japanese Patent Unexamined Publication No. 1-207223), the dissolving temperature of N-acylamino acid in a liquid oil is as high as about 100° C., which causes deterioration in quality of other oils combined therewith. Further, the resulting gel composition have a high viscosity and a poor thixotropic property. It is difficult to obtain a high thixotropic gel even at low temperatures, and the problem of oil separation with time is encountered.

Furthermore, in the combination of the dextrin ester of the fatty acid, organic montmorillonite, etc. (Japanese Patent Unexamined Publication No. 61-56115), there is a restriction on compounding for obtaining a gel composition, and the thixotropic property of the resulting gel composition is not sufficient.

Also for the dextrin esters of fatty acids, various attempts have been made for improvements such as changes in the substitution degree of fatty acids per glucose, and use of the dextrin esters of mixed fatty acids obtained by concurrently reacting different straight chain fatty acids having 12 to 22 carbon atoms (Japanese Patent Unexamined Publication No. 1-203319). However, with respect to the properties of gel compositions or viscous compositions obtained thereby, the softness and the smoothness of gels have been improved to some degrees, but particularly, the thixotropic property has not been sufficiently improved.

A gelling agent is therefore desired which provides a high thixotropic gel composition or a high thixotropic viscous composition in a simple system.

SUMMARY OF THE INVENTION

In view of the above situation, the present inventors conducted intensive investigations. As a result, the present inventors discovered that a dextrin ester of fatty acids obtained by esterifying dextrin having a specific average saccharide polymerization degree with the mixed fatty acids comprising a straight chain fatty acid having a specific numbers of carbon atoms and at least one fatty acid selected from the groups consisting of branched fatty acids, unsaturated fatty acids and straight chain saturated fatty acids having 6 or less carbon atoms was useful as a gelling agent for a liquid oil, and particularly useful as a high thixotropic gelling agent, which could give a similar thixotropic effect to hydrocarbon solvents having branched chains such as isoparaffins. Further, the present inventors discovered that the dextrin ester of the present invention was also excellent in the moisture retaining property, emulsifiability, adhesion and dispersibility, and also discovered that a composition containing the dextrin ester of fatty acids of the present invention together with at least one liquid oil and/or solvent was good in temperature stability, had a high thixotropic property and a good usability, thus completing the present invention.

The present invention provides (1) a dextrin ester of fatty acids in which dextrin has an average saccharide polymerization degree of 3 to 150, the fatty acids comprise a straight chain fatty acid having 8 to 22 carbon atoms and at least one fatty acid selected from the group consisting of branched fatty acids having 4 to 26 carbon atoms, unsaturated fatty acids having 6 to 30 carbon atoms and straight chain saturated fatty acids having 6 or less carbon atoms, and the substitution degree of fatty acids per glucose unit is 1.0 to 3.0; (2) the dextrin ester of fatty acids of (1) in which the average saccharide polymerization degree of dextrin is 10 to 100; (3) the dextrin ester of fatty acids of (1) or (2), in which the substitution degree of fatty acids per glucose unit is 1.2 to 2.8; (4) the dextrin ester of fatty acids of anyone of (1) to (3) in which the molar ratio of the straight chain fatty acid having 8 to 22 carbon atoms to at least one fatty acid selected from the group consisting of the branched fatty acids, the unsaturated fatty acids and the straight chain saturated fatty acids having 6 or less carbon atoms is within the range of 50:50 to 99:1 in fatty acid composition thereof; (5) the dextrin ester of fatty acids of (4) in which the molar ratio is 70:30 to 99:1; (6) a gelling agent which is consisted of the dextrin ester of fatty acids of anyone of (1) to (5); (7) a composition comprising the dextrin esters of fatty acids of anyone of (1) to (5) and at least one liquid oil and/or solvent; and (8) a composition for a drug, a cosmetic, a quasidrug, a coating or a base for ink comprising the dextrin ester of fatty acids of anyone of claims (1) to (5).

DESCRIPTION OF THE PREFERRED EMBODIMENTS

Figure 1:
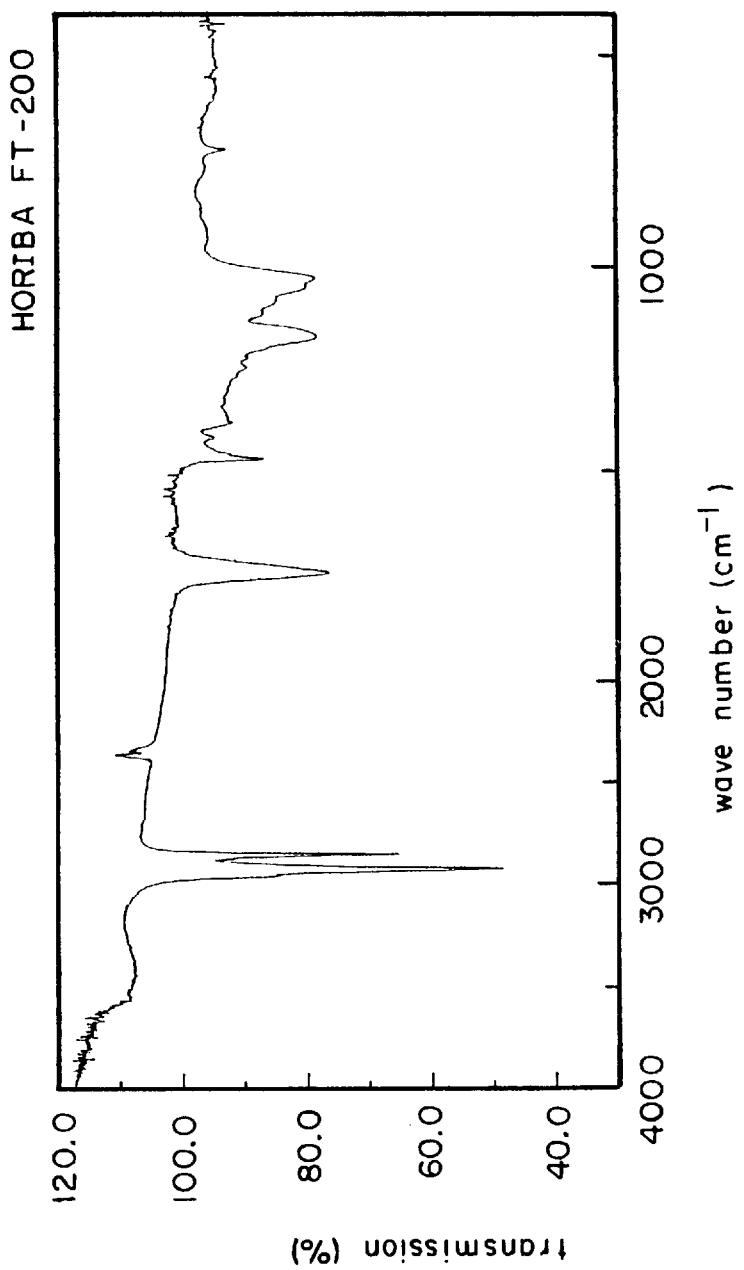
FIG. 1 shows an IR spectrum of a dextrin ester of fatty acids (Production Example 1) of the present invention.

The present invention will hereinafter be described in more detail.

Dextrin used in the present invention has an average saccharide polymerization degree of 3 to 150, preferably 10 to 100. When the average saccharide polymerization degree is less than 3, a dextrin ester of fatty acids becomes wax-like, resulting in difficulty in obtaining a smooth gel. On the other hand, when the average saccharide polymerization degree exceeds 150, the dissolving temperature of a dextrin ester of fatty acids in a liquid oil is elevated or the solubility becomes poor in some cases. The saccharide chains may be straight or branched.

The straight chain fatty acids used in the present invention are straight chain saturated fatty acids having 8 to 22 carbon atoms, and examples thereof include caprylic acid, capric acid, lauric acid, myristic acid, palmitic acid, stearic acid, arachic acid and behenic acid. They may be used alone or in combination.

A straight chain fatty acid having 7 or less carbon atoms is difficult to form a gel, whereas a straight chain fatty acid having 23 or more carbon atoms makes a gel cloudy and results in difficulty in obtaining the smoothness.

The branched fatty acids used in the present invention are branched saturated fatty acids having 4 to 26 carbon atoms, and examples thereof include isobutyric acid, isovaleric acid, 2-ethylbutyric acid, ethylmethylacetic acid, isoheptanoic acid, 2-ethylhexanoic acid, isononanoic acid, isodecanoic acid, isotridecanoic acid, isomyristic acid, isopalmitic acid, isostearic acid, isoarachic acid and isohexacosanoic acid. They may be used alone or in combination.

The unsaturated fatty acids used in the present invention are unsaturated fatty acids having 6 to 30 carbon atoms. Examples of monoene unsaturated fatty acids include cis-4-decenoic (obtusilic) acid, 9-decenoic (caproleic) acid, cis-4-dodecenoic (linderic) acid, cis-4-tetradecenoic (tsuzuic) acid, cis-5-tetradecenoic (physeteric) acid, cis-9-tetradecenoic (myristoleic) acid, cis-6-hexadecenoic acid, cis-9-hexadecenoic (palmitoleic) acid, cis-9-octadecenoic (oleic) acid, trans-9-octadecenoic (elaidic) acid, cis-11-octadecenoic (asclepinic) acid, cis-11-eicosenoic (gondoleic) acid, cis-17-hexacosenoic (ximenic) acid and cis-21-triacontenoic (lumequenic) acid. Examples of polyene unsaturated fatty acids include sorbic acid, linoleic acid, hiragoic acid, punicic acid, linolenic acid, γ-linolenic acid, moroctic acid, stearidonic acid, arachidonic acid, EPA, clupanodonic acid, DHA, herring acid, stearolic acid, crepenic acid and ximenynic acid. They may be used alone or in combination.

The straight chain saturated fatty acids each having 6 or less carbon atoms used in the present invention include caproic acid, valeric acid, butyric acid, propionic acid and acetic acid. They may be used alone or in combination.

Examples of combinations of the fatty acids esterifying dextrin include a combination of a straight chain fatty acid having 8 to 22 carbon atoms and a branched fatty acid having 4 to 26 carbon atoms, a combination of said straight chain fatty acid and an unsaturated fatty acid having 6 to 30 carbon atoms, a combination of said straight chain fatty acid and a straight chain saturated fatty acid having 6 or less carbon atoms, a combination of said straight chain fatty acid, said branched fatty acid and said unsaturated fatty acid, a combination of said straight chain fatty acid, said branched fatty acid and said straight chain saturated fatty acid having 6 or less carbon atoms, a combination of said straight chain fatty acid, said unsaturated fatty acid and said straight chain saturated fatty acid having 6 or less carbon atoms, and a combination of said straight chain fatty acid, said branched fatty acid, said unsaturated fatty acid and said straight chain saturated fatty acid having 6 or less carbon atoms.

Examples of the dextrin esters of fatty acids of the present invention include the following esters:

Dextrin ester of caprylic acid/isobutyric acid,.

Dextrin ester of caprylic acid/2-ethylhexanoic acid,

Dextrin ester of caprylic acid/isoarachic acid,

Dextrin ester of caprylic acid/linoleic acid,

Dextrin ester of caprylic acid/acetic acid,

Dextrin ester of caprylic acid/isopalmitic acid/butyric acid,

Dextrin ester of caprylic acid/palmitic acid/oleic acid,

Dextrin ester of caprylic acid/oleic acid/acetic acid,

Dextrin ester of lauric acid/ethylmethylacetic acid,

Dextrin ester of lauric acid/2-ethylhexanoic acid,

Dextrin ester of lauric acid/obtusilic acid,

Dextrin ester of lauric acid/caproic acid,

Dextrin ester of lauric acid/linolenic acid/propionic acid,

Dextrin ester of lauric acid/behenic acid/isoheptanoic acid,

Dextrin ester of myristic acid/isostearic acid,

Dextrin ester of myristic acid/isohexacosanoic acid,

Dextrin ester of myristic acid/arachidonic acid,

Dextrin ester of palmitic acid/2-ethylhexanoic acid,

Dextrin ester of palmitic acid/isostearic acid,

Dextrin ester of palmitic acid/oleic acid,

Dextrin ester of palmitic acid/isovaleric acid/isostearic acid,
Dextrin ester of palmitic acid/isononanoic acid/caproic acid,
Dextrin ester of palmitic acid/stearic acid/2-ethylhexanoic acid,
Dextrin ester of palmitic acid/stearic acid/caproic acid/acetic acid,
Dextrin ester of stearic acid/isopalmitic acid,
Dextrin ester of stearic acid/oleic acid,
Dextrin ester of stearic acid/physeteric acid/EPA,
Dextrin ester of stearic acid/asclepinic acid/acetic acid,
Dextrin ester of arachic acid/stearolic acid,
Dextrin ester of arachic acid/butyric acid,
Dextrin ester of behenic acid/2-ethylbutyric acid,
Dextrin ester of behenic acid/linderic acid, and
Dextrin ester of behenic acid/caproic acid/valeric acid.

The substitution degree of fatty acids to dextrin used in the present invention is 1.0 to 3.0 per glucose unit, and preferably 1.2 to 2.8 per glucose unit. When the substitution degree is less than 1.0, the dissolving temperature of dextrin in a liquid oil, etc. is increased to a high temperature of 100° C. or more, unfavorably resulting in coloring and development of peculiar odors.

In the fatty acid composition of the dextrin ester of fatty acid of the present invention, the molar ratio of the straight chain fatty acid having 8 to 22 carbon atoms to at least one fatty acid selected from the group consisting of the branched fatty acids, the unsaturated fatty acids and the straight chain saturated fatty acids having 6 or less carbon atoms is preferably 50:50 to 99:1, and more preferably 60:40 to 99:1, and further preferably 70:30 to 99:1, because of more noticeable effects of the present invention.

Methods for producing the dextrin esters of fatty acids of the present invention will be illustrated below.

In the present invention, acid halides, acid anhydrides, etc. of the straight chain fatty acids, branched fatty acids, the unsaturated fatty acids and the fatty acids each having 6 or less carbon atoms are used for esterification of the above-mentioned dextrin.

First, the dextrin is dispersed in a reaction solvent, and a catalyst is added thereto as required. The acid halides or the acid anhydrides of the straight chain fatty acid and at least one fatty acid selected from the group consisting of branched fatty acids, the unsaturated fatty acids and the fatty acids having 6 or less carbon atoms are added thereto to allow them to react. In this case, these fatty acids may be mixed and concurrently added to allow them to react, or the fatty acid low in reactivity such as the branched fatty acid or the unsaturated fatty acid may first be allowed to react, and subsequently the straight chain fatty acid is added to allow it to react. Of these, the preferred method can be employed in production.

The reaction solvents which can be used include formamide compounds such as dimethylformamide and formamide, acetamide compounds, ketone compounds, aromatic compounds such as benzene, toluene and xylene, and dioxane.

The reaction catalysts which can be used include tertiary amino compounds such as pyridine and picoline.

Although the reaction temperature is appropriately selected depending on the fatty acids as starting materials, it is preferably 0° to 100° C.

Then, the composition comprising the novel dextrin ester of fatty acids of the present invention will be illustrated in detail.

When the novel dextrin ester of fatty acids of the present invention is compounded into the composition, the amount of the fatty acids compounded is preferably 0.1 to 90% by weight (hereinafter briefly referred to as %), and more preferably 0.5 to 50%, though there is no particular restriction on the amount.

Examples of the lubricants used in the compositions include hydrocarbon oils such as liquid paraffins, isoparaffins, squalane and vaseline; ester oils such as glyceryl tri-2-ethylhexanoate, glyceryl tri(caprylate caprate), diglyceryl mono-, di-, tri-, tetra-isostearate, neopentyl glycol dioctanoate, neopentyl glycol dicaprate, isopropyl myristate, butyl stearate, 2-ethylhexyl palmitate, isononyl isononanoate, isotridecyl isononanoate, stearyl stearate, isostearyl myristate, octyldodecyl myristate, octyldodecyl oleate and cholesteryl 12-hydroxystearate; higher fatty acids such as capric acid, lauric acid, myristic acid, palmitic acid, stearic acid, oleic acid, behenic acid, isostearic acid, erucic acid, linoleic acid and linolenic acid; higher alcohols such as octyl alcohol, decyl alcohol, lauryl alcohol, myristyl alcohol, cetyl alcohol, stearyl alcohol, behenyl alcohol, 2-hexyldecanol, 2-octyldecanol, oleyl alcohol and isostearyl alcohol; animal and plant oils such as olive oil, tsubaki oil, soybean oil, cottonseed oil, sesame oil, safflower oil, wheat embryo oil, coix seed oil, rice oil, jojoba oil, caster oil, linseed oil, corn oil, rapeseed oil, coconut oil, palm oil, squalene, liquid lanolin, mink oil, yolk oil and wool oil; waxes such as paraffin wax, microcrystalline wax, ceresine wax, beeswax, carnauba wax, candelilla wax, hydrogenated caster oil and rosin, and silicone oils such as dimethylpolysiloxane, cyclic silicone, methylphenylpolysiloxane and modified silicone. Examples of the organic solvents which can be used include aromatic compounds such as benzene, toluene and xylene, chlorine compounds such as chloroform, dichloromethane and dichloroethane, ether compounds such as dioxane and tetrahydrofuran, benzyl alcohol, phenoxyethanol, carbitols, cellosolves, polybutene and spindle oil.

In the present invention, other additives may be added to the compositions to a degree that the characteristics of the desired compositions are not impaired. Such additives include anionic surfactants, cationic surfactants, amphoteric surfactants, nonionic surfactants, drugs, ultraviolet ray absorbing agents, moisture retaining agents, preservatives, antioxidants, powders of titanium oxide, mica, kaolin, talc, iron oxide, ultramarine, cobalt titanate, etc., powders thereof subjected to treatment for making them hydrophobic, organic pigments, dyes, perfumes, lower alcohols such as methyl alcohol and ethyl alcohol, and water.

The compositions comprising the novel dextrin esters of fatty acids of the present invention have an excellent thixotropic property, and further, are also excellent in the moisture retaining property, emulsifiability, adhesion and dispersibility. Accordingly, the compositions are excellently used for drugs, cosmetics, quasi-drugs, printing ink, ball pen ink, coatings and coloring materials.

The present invention will described with reference to the following examples in more detail, but is not limited thereby.

Methods for analysis used in the following examples were as follows:

IR Analysis
FT-IR: Measured by the KBr tablet method using an FT-200 spectrometer (Horiba, Ltd.).
HPLC Analysis
HPLC Instrument: Waters, Model 510
Detector: RI (differential refractometer)

Column: Shiseido Co., Ltd., Capsule Pack C18 (4.6 mm in diameter×250 mm)

Eluent: Acetonitrile

Method of Measurement: After alkali decomposition of a sample, fatty acids were extracted, and induction was conducted with p-bromophenacyl bromide to make an HPCL measurement.

Preparation of Shear Stress-Shear Rate Curve (Measurement of Thixotropic Property)

Measuring Instrument: Toki Sangyo Co., Ltd., R100 type viscometer (RE1OOL type, rotor No. 2 was used.)

After allowing an isoparaffin gel containing 10% sample to stand for 24 hours, the shear stress to the shear rate was measured by use of the above-mentioned measuring instrument at a temperature of 20° C.

Production Example 1 Dextrin Ester of Palmitic Acid/2-Ethylhexanoic Acid

In a mixed solvent of 200 g of dimethylformamide and 130 g of pyridine, 32.4 g of dextrin having an average saccharide polymerization degree of 30 was dispersed at 70° C., and mixed fatty acid chlorides of 98 g of palmitic acid chloride and 17 g of 2-ethylhexanoic acid chloride (reaction molar ratio: 2.1, straight fatty acid/branched fatty acid=75/25) were added dropwise thereto for 20 minutes. After termination of dropping, the reaction temperature was elevated to 90° C. to conduct reaction for 15 hours. The reaction solution was precipitated in methanol and filtered. The solid materials were washed with methanol, and then dried to obtain 90 g of a white powder.

FIG. 1 shows an IR spectrum of the resulting dextrin ester of fatty acids. From this spectrum, an ester-derived peak was confirmed at 1740 $cm^{-1}$, and alkyl-derived peaks were confirmed at 2800 to 3000 $cm^1$. Further, from the HPLC analysis of the fatty acids after alkali decomposition, the substitution degree was confirmed to be 1.6, and the composition of palmitic acid/2-ethylhexanoic acid was confirmed to be 87/13. The melting temperature (the temperature at which melting was initiated) was 49° C.

Figure 2:
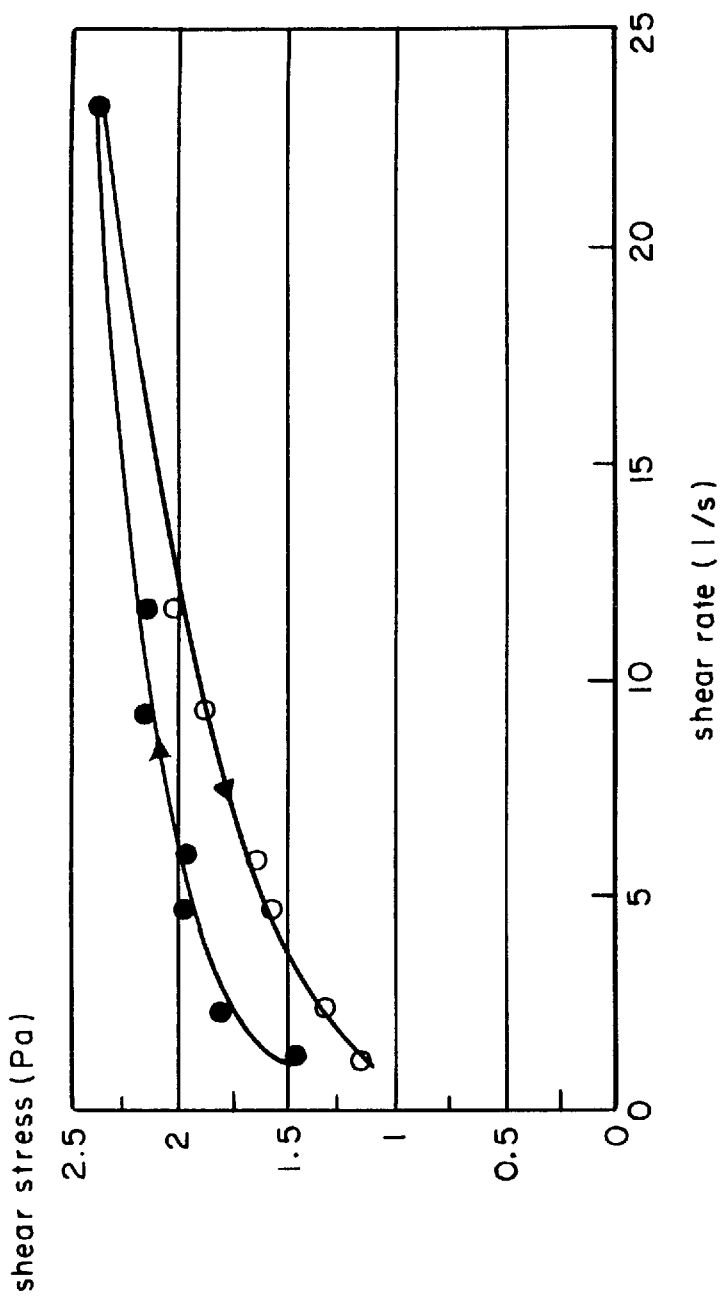
FIG. 2 is a graph showing that the dextrin ester of fatty acids (Production Example 1) of the present invention has a thixotropic property.

FIG. 2 is a graph showing the thixotropic property of the resulting dextrin ester of palmitic acid/2-ethylhexanoic acid. In FIG. 2, the numbers on the ordinate indicate the shear stress, and the numbers on the abscissa indicate the shear rate. The shear stress increases as the shear rate increases, and when the shear rate is decreased from the point at which the shear stress has reached the maximum, the shear stress descends along the ascent curve. This shows the thixotropic property. The closer spacing between the ascent curve and the descent curve shows that the thixotropic property is excellent, namely that the dextrin ester of fatty acids is excellent in the thixotropic property.

Production Example 2 Dextrin Ester of Stearic Acid/Oleic Acid

In a mixed solvent of 200 g of dimethylformamide and 90 g of pyridine, 32.4 g of dextrin having an average saccharide polymerization degree of 100 was dispersed at 70° C., and 34 g of oleic acid chloride was added dropwise for 5 minutes. After termination of dropping, reaction was conducted for 2 hours, and then 51 g of stearic acid chloride was added dropwise for 10 minutes (reaction molar ratio: 1.4, straight fatty acid/branched fatty acid=60/40). After termination of dropping, the reaction temperature was elevated to 90° C. to conduct reaction for 3 hours. The reaction solution was precipitated in methanol and filtered. The solid materials were washed with methanol, and then dried to obtain 78 g of a white powder.

From an IR spectrum, an ester-derived peak was confirmed at 1740 $cm^{-1}$, and alkyl-derived peaks were confirmed at 2800 to 3000 $cm^{-1}$. Further, from the HPLC analysis of the fatty acids after alkali decomposition, the substitution degree was confirmed to be 1.0, and the composition of stearic acid/oleic acid was confirmed to be 65/35. The melting temperature was 52° C.

Production Example 3 Dextrin Ester of Lauric Acid/Caproic Acid

In a mixed solvent of 200 g of dimethylformamide and 190 g of pyridine, 32.4 g of dextrin having an average saccharide polymerization degree of 5 was dispersed at 70° C., and mixed fatty acid chlorides of 121 g of lauric acid chloride and 4 g of caproic acid chloride (reaction molar ratio: 2.9, lauric acid/caproic acid=95/5) were added dropwise thereto for 30 minutes. After termination of dropping, the reaction temperature was elevated to 90° C. to conduct reaction for 5 hours. The reaction solution was precipitated in methanol and filtered. The solid materials were washed with methanol, and then dried to obtain 116 g of a white powder.

From an IR spectrum, an ester-derived peak was confirmed at 1740 $cm^{-1}$, and alkyl-derived peaks were confirmed at 2800 to 3000 $cm^{-1}$. Further, from the HPLC analysis of the fatty acids after alkali decomposition, the substitution degree was confirmed to be 2.4, and the composition of lauric acid/caproic acid was confirmed to be 93/7. The melting temperature was 46° C.

EXAMPLE 1

An emulsion (O/W) having the following composition was prepared using the dextrin ester of fatty acids obtained in Production Example 2.

| | |
|---|---|
| 1. Polyoxyethylenesorbitan monostearate (20 E. O.) | 1.0% |
| 2. Polyoxyethylenesorbitol tetraoleate (60 E. O.) | 0.5% |
| 3. Glyceryl monostearate | 1.0% |
| 4. Stearic acid | 0.5% |
| 5. Behenyl alcohol | 0.5% |
| 6. Liquid paraffin | 4.0% |
| 7. Glyceryl trioctanoate | 4.0% |
| 8. Cetyl 2-ethylhexanoate | 2.0% |
| 9. Dextrin ester of stearic acid/oleic acid (Production Example 2) | 3.0% |
| 10. 1,3-Butylene glycol | 5.0% |
| 11. Carboxyvinyl polymer | 0.05% |
| 12. Sodium hydroxide | 0.025% |
| 13. Preservative | suitable amount |
| 14. Perfume | suitable amount |
| 15. Purified water | the balance |

(Preparation)

(A) Components 10 to 13 and a part of component 15 were homogeneously dissolved by heating at 70° C.

(B) Components 1 to 9 were homogeneously melted by heating at 70° C.

(C) (B) was added to (A), followed by emulsification.

(D) Component 11 and the remainder of component 15 were added to (C), and the mixture was cooled. Then, component 14 was added thereto to obtain an emulsion.

The above-mentioned emulsion was fit to a skin and excellent in wet feeling.

EXAMPLE 2

W/O cream having the following composition was prepared using the dextrin ester of fatty acids obtained in Production Example 1.

| | |
|---|---:|
| 1. Sorbitan sesquioleate | 3.0% |
| 2. Glyceryl monostearate | 4.0% |
| 3. Polyethylene glycol monostearate (40 E.O.) | 2.0% |
| 4. Cetyl alcohol | 2.0% |
| 5. Dextrin ester of palmitic acid/2-ethylhexanoic acid (Production Example 1) | 15.0% |
| 6. Squalane | 3.0% |
| 7. 1,3-Butylene glycol | 10.0% |
| 8. Preservative | suitable amount |
| 9. Perfume | suitable amount |
| 10. Purified water | the balance |

(Preparation)

(A) Components 1 to 6 were homogeneously melted by heating at 70° C.

(B) Components 7, 8 and 10 were homogeneously dissolved by heating at 70° C.

(C) (B) was added to (A), followed by emulsification. After cooling, component 9 was added thereto to obtain cream.

The above-mentioned cream was excellent in spreadability and fitting to a skin, and good in aging stability.

EXAMPLE 3

A foundation having the following composition was prepared using the dextrin ester of fatty acids obtained in Production Example 3.

| | |
|---|---:|
| 1. Dextrin ester of lauric acid/caproic acid (Production Example 3) | 13.0% |
| 2. Dextrin palmitate (trade name: Leopearl KL, manufactured by Chiba Flour Milling Co., Ltd.) | 2.0% |
| 3. Ceresine | 8.0% |
| 4. Liquid paraffin | the balance |
| 5. Methylphenylpolysiloxane | 9.0% |
| 6. Perfume | suitable amount |
| 7. Coloring material | suitable amount |

(Preparation)

(A) Components 1 to 5 were homogeneously melted by heating at 70° C.

(B) Component 7 was added to (A), and homogeneously dispersed. Component 6 was further added thereto to obtain a foundation.

The above-mentioned foundation was excellent in spreadability and endurance, and good in aging stability.

EXAMPLE 4

A lipstick having the following composition was prepared using the dextrin ester of fatty acids obtained in Production Example 1.

| | |
|---|---:|
| 1. Microcrystalline wax | 5.0% |
| 2. Fatty acid ester of dipentaerythrite | 5.0% |
| 3. Polybutene | 10.0% |
| 4. Octyldodecyl lanolate | 30.0% |
| 5. Cetyl 2-ethylhexanoate | 10.0% |
| 6. Dextrin ester of palmitic acid/2-ethylhexanoic acid (Production Example 1) | 20.0% |
| 7. Diglycerol triisostearate | 12.0% |
| 8. Coloring material | suitable amount |
| 9. Perfume | suitable amount |

(Preparation)

(A) Components 1 to 9 were melted by heating, and kneaded by use of a roll-mill. The resulting mixture was poured into a container, and cooled to obtain a lipstick.

The above-mentioned lipstick was excellent in spreadability and adhesion, and good in aging stability.

EXAMPLE 5

Eye liner having the following composition was prepared using the dextrin ester of fatty acids obtained in Production Example 1.

| | |
|---|---:|
| 1. Microcrystalline wax | 6.0% |
| 2. Carnauba wax | 4.0% |
| 3. Dextrin ester of palmitic acid/2-ethylhexanoic acid (Production Example 1) | 20.0% |
| 4. Silicone graft polymer (solid) | 4.0% |
| 5. Organic bentonite | 1.5% |
| 6. Silicic acid anhydride | 1.5% |
| 7. Propylene carbonate | 0.5% |
| 8. Low boiling isoparaffin hydrocarbon oil | the balance |
| 8. Coloring material | suitable amount |

(Preparation)

(A) Components 1 to 9 were melted by heating, and treated with a roll-mill to obtain eye liner.

The above-mentioned eye liner was excellent in film forming property and spreadability, and good in aging stability.

EXAMPLE 6

Mascara having the following composition was prepared using the dextrin ester of fatty acids obtained in Production Example 2.

| | |
|---|---:|
| 1. Stearic acid | 2.0% |
| 2. Beeswax | 3.0% |
| 3. Cetanol | 1.0% |
| 4. Dextrin ester of stearic acid/oleic acid (Production Example 2) | 10.0% |
| 5. Polyoxyethylenesorbitan monooleate (20 E. O.) | 1.0% |
| 6. Sorbitan sesquioleate | 0.5% |
| 7. Coloring material | suitable amount |
| 8. Triethanolamine | 1.0% |
| 9. Preservative | suitable amount |
| 10. Polyacrylate emulsion | 40.0% |
| 11. Purified water | the balance |

(Preparation)

(A) Components 1 to 6 were homogeneously melted by heating at 70° C., and component 7 was added thereto. Then, the mixture was homogeneously mixed.

(B) Components 8 to 11 were homogeneously dissolved by heating at 70° C.

(C) (B) was added to (A) and emulsified, followed by cooling. A container was filled with the product to obtain mascara.

The above-mentioned mascara was excellent in film forming property and good in endurance.

EXAMPLE 7

Printing ink having the following composition was prepared using the dextrin ester of fatty acids obtained in Production Example 1.

| | |
|---|---:|
| 1. Dextrin ester of palmitic acid/2-ethylhexanoic acid (Production Example 1) | 2.0% |
| 2. Carbon black (MA-8, Mitsubishi Kasei Corp.) | 20.0% |

-continued

| | |
|---|---|
| 3. Alkali blue toner paste (C. I. 42750:1) | 4.0% |
| 4. Phthalocyanine blue (JIS K 5241) | 2.0% |
| 5. Phenol resin varnish (Hitanol 1501, Hitachi Chemical Co., Ltd.) | 45.0% |
| 6. Linseed oil varnish (JIS K 5421 | 12.0% |
| 7. Liquid paraffin (Silkool P-70, Matsumura Sekiyu Co.) | 13.0% |
| 8. Manganese dryer (JIS K 8997-64, Nihon Kagaku Sangyo Co., Ltd.) | 2.0% |

(Preparation)

(A) Components 1 and 7 were melted by heating at 80° C.

(B) Components 2 to 6 and 8 were in turn added to (A), and the mixture was well kneaded at room temperature to prepare a plate ink.

The above-mentioned plate ink was excellent in dispersion stability, and excellent in printing characteristics. Namely, the ink gave suitable viscosity in printing, showed the thixotropic property, and could be transferred as a homogeneous thin film to a plate.

EXAMPLE 8

A white oil coating for metal having the following composition was prepared using the dextrin ester of fatty acids obtained in Production Example 2.

| | |
|---|---|
| 1. Dextrin ester of stearic acid/oleic acid (Production Example 2) | 1.5% |
| 2. Titanium white (MT 500B, Tayca Corp.) | 60.0% |
| 3. Dehydrated caster oil-modified alkyd resin varnish | 33.0% |
| 4. Liquid paraffin (Silkool P-70, Matsumura Sekiyu Co.) | 5.0% |
| 5. Manganese dryer (JIS K 8997-64, Nihon Kagaku Sangyo Co., Ltd.) | 0.5% |

(Preparation)

(A) Components 1 and 4 were melted by heating at 80° C., and components 3, 2 and 5 were in turn added thereto. Then, the mixture was well kneaded at room temperature to prepare a white oil coating for metal.

The above-mentioned white oil coating for metal was excellent in dispersion stability. Further, the oil coating was largely decreased in viscosity by adding a small amount of oil or solvent and stirring the mixture at the time of use, resulting in viscosity suitable for coating operations. In the case of brushing, the oil coating was easily spread in coating, could be applied thick, hardly gave brush marks, and generated no drips. Thus, this oil coating was excellent in viscosity as a coating.

The dextrin esters of fatty acids of the present invention have an excellent thixotropic property, and are also excellent in the moisture retaining property, emulsifiability, adhesion and dispersibility. Accordingly, the compositions comprising the dextrin esters of fatty acids are excellent in storage stability and usage, and excellent for cosmetics, printing ink, coatings, etc.

What is claimed is:

1. A dextrin ester of fatty acids in which dextrin has an average glucose polymerization degree of 3 to 150, the fatty acids comprise a straight chain fatty acid having 8 to 22 carbon atoms and at least one fatty acid selected from the group consisting of branched fatty acids each having 4 to 26 carbon atoms, unsaturated fatty acids each having 6 to 30 carbon atoms and straight chain saturated fatty acids each having 6 or less carbon atoms, and the degree of substitution of fatty acids per glucose unit is 1.0 to 3.0.

2. The dextrin ester of fatty acids according to claim 1, in which the average glucose polymerization degree of dextrin is 10 to 100.

3. The dextrin ester of fatty acids according to claim 1 or 2, in which the degree of substitution of fatty acids per glucose unit is 1.2 to 2.8.

4. The dextrin ester of fatty acids according to claim 1, in which the molar ratio of the straight chain fatty acid having 8 to 22 carbon atoms to at least one fatty acid selected from the group consisting of the branched fatty acids, the unsaturated fatty acids and the straight chain saturated fatty acids having 6 or less carbon atoms is within the range of 50:50 to 99:1 in fatty acid composition thereof.

5. The dextrin ester of fatty acids according to claim 4, in which the molar ratio of the straight chain fatty acid having 8 to 22 carbon atoms to at least one fatty acid selected from the group consisting of the branched fatty acids, the unsaturated fatty acids and the straight chain saturated fatty acids having 6 or less carbon atoms is within the range of 60:40 to 99:1 in fatty acid composition thereof.

6. A gel comprising a liquid oil or a solvent and a gelling agent which consists of a dextrin ester of fatty acids wherein the dextrin ester comprises a dextrin having an average glucose polymerization degree of 3 to 150 and fatty acids comprising a straight chain fatty acid having 8 to 22 carbon atoms and at least one fatty acid selected from the group consisting of (a) branched fatty acids each having 4 to 26 carbon atoms, (b) unsaturated fatty acids each having 6 to 30 carbon atoms, and (c) straight chain saturated fatty acids each having 6 or less carbon atoms, and the degree of substitution of fatty acids per glucose unit is 1.0 to 3.0.

7. A composition comprising the dextrin esters of fatty acids of claims 1 or 5 and at least one liquid oil and/or solvent.

8. A base for a drug, a cosmetic, a coating or an ink, said base comprising a liquid oil or a solvent and a dextrin ester of fatty acids wherein the dextrin ester comprises a dextrin having an average glucose polymerization degree of 3 to 150 and fatty acids comprising a straight chain fatty acid having 8 to 22 carbon atoms and at least one fatty acid selected from the group consisting of (a) branched fatty acids each having 4 to 26 carbon atoms, (b) unsaturated fatty acids each having 6 to 30 carbon atoms, and (c) straight chain saturated fatty acids each having 6 or less carbon atoms, and the degree of substitution of fatty acids per glucose unit is 1.0 to 3.0.

9. A base for cosmetics in accord with claim 8, further including a cosmetic additive.

10. A base for cosmetics in accord with claim 9, wherein the additive is selected from the group consisting of a perfume, a preservative, a coloring material, an ultraviolet ray absorbing agent and a moisture retaining agent.

11. A base for a drug in accord with claim 8, further including a drug.

12. A base for an ink or a coating in accord with claim 8, further including a pigment or a dye.

* * * * *